United States Patent [19]
Znaiden et al.

[11] Patent Number: 5,268,176
[45] Date of Patent: Dec. 7, 1993

[54] METHOD AND COMPOSITIONS FOR THE NON-INVASIVE TREATMENT OF TELANGIECTASIA

[75] Inventors: Alexander P. Znaiden, Sloatsburgh, N.Y.; George P. Serban, Ridgefield, Conn.

[73] Assignee: Avon Products, Inc., New York, N.Y.

[21] Appl. No.: 733,707

[22] Filed: Jul. 22, 1991

[51] Int. Cl.⁵ .............................................. A61K 6/00
[52] U.S. Cl. ..................... 424/401; 514/103; 424/445
[58] Field of Search .................. 424/485, 401, 449; 514/103

[56] References Cited

U.S. PATENT DOCUMENTS

| | | | |
|---|---|---|---|
| 3,887,703 | 6/1975 | Manoussos et al. | 514/880 |
| 4,859,847 | 12/1989 | Kligman et al. | 514/171 |
| 4,952,396 | 8/1990 | Sabin et al. | 514/103 |
| 5,019,569 | 5/1991 | Kligman et al. | 524/171 |
| 5,023,235 | 6/1991 | N'Guyen et al. | 424/59 |

Primary Examiner—Thurman K. Page
Assistant Examiner—Leon R. Horne
Attorney, Agent, or Firm—Hopgood, Calimafde

[57] ABSTRACT

This invention is directed to a non-invasive, topical treatment for telangiectasia, a dermatological condition commonly known as spider veins. The treatment preferably includes repeated applications of a composition having an effective amount of an inositol phosphoric acid or derivatives and mixtures thereof. Inositol hexaphosphate (phytic acid) is most preferred, with or without the use of a compression stocking.

9 Claims, 2 Drawing Sheets

METHOD AND COMPOSITIONS FOR THE NON-INVASIVE TREATMENT OF TELANGIECTASIA

BACKGROUND OF THE INVENTION

Field of the Invention

This invention relates to a method and compositions for the topical treatment of telangiectasia, otherwise known as spider veins, and particularly the application of an effective amount of a low molecular weight organic acid.

The State of the Art

Telangiectasia is an art-recognized condition characterized by the visual dilation of one or several superficial skin arterioles in the human body. A number of physiological circumstances may contribute to the formation of these aberrant arterioles and, in some cases, they are the symptomatic of a systemic, pathological disorder. Spider veins normally occur in about 15 percent of the population as a cosmetic manifestation not prompted by a specific ailment. The likelihood of developing this condition increases with age. Spider veins are aesthetically displeasing, especially when the affected vessels are located on the face, upper trunk, lower leg, or other normally visible parts of the body.

The morphological characteristics of an arteriole spider vein are shown in FIG. 1. Typically, a spider vein originates with dilated portion (OR) of main feeding vessel (FV) which protrudes and presses against the underside of epidermis (EP). Extending from main feeding vessel (FV) are lateral arms (LA) which branch off to capillary bed (CB) and eventually join venous return flow vessels (VR). Spider veins are readily visible because origin (OR) is proximate to the skin surface.

More particularly, dilated arterioles are readily observed based on their characteristic shape and irritated red color caused by oxygenated blood flowing close to the surface of the skin. The dilated vessels typically blanch when pressure is applied to reduce blood flow from a larger circulatory vessel.

Known techniques for the treatment of spider veins involve invasive procedures which are intended to disrupt or destroy the anatomy of the arteriole by injecting a sclerosing agent into an adjacent artery. Typical sclerosing agents include hypertonic saline and octadocanol. These prior art techniques are undesirable because they require delicate operations which must be performed under the supervision of a licensed dermatologist.

An alternative art-recognized technique employs a laser beam focused on the offending vessel for the purpose of disrupting and destroying the affected portions. Spider veins have also been "treated" with pigmented creams intended to mask the condition from visual observation. It will be appreciated that this cosmetic application has no therapeutic value, unlike the remedial method and compositions of the present invention.

OBJECTS OF THE INVENTION

It is an object of the present invention to provide topically applied compositions for the treatment of telangiectasia.

It is an additional object of the present invention to provide a simplified, non-invasive, therapeutic technique for the treatment of telangiectasia.

It is a further object of the present invention to provide an over-the-counter formulation which is readily available to the retail consumer.

Yet another object of the present invention is to provide a method for treating spider veins using a topically applied composition in conjunction with a compression stocking or bandage on the affected area.

It is a further object of the present invention to provide a composition for the topical treatment of telangestasia which comprises an effective amount of an inositol phosphoric acid or derivatives and mixtures thereof.

Another object of the present invention is to provide a prepared composition which can be topically applied without the attention of a licensed physician.

SUMMARY OF THE INVENTION

The present invention provides a method for treating telangiectasia (spider veins) with effective amounts of topically applied compositions containing at least one inositol phosphoric acid or derivatives and mixtures thereof. Generally, inositol phosphoric acids are the phosphorylated derivatives of inositol. The hexaphosphate derivative, also known as phytic acid, is most preferred. The method of treatment generally comprises daily application of an effective composition for two to fourteen days, depending on concentration of the active ingredient, and the number and size of the offending vessels.

DETAILED DESCRIPTION OF PREFERRED EMBODIMENTS

The present invention is specifically directed to a non-invasive method for the therapeutic treatment of spider veins. This method involves the topical application of a lotion, cream, ointment, or other composition containing one or a combination of effective compounds. Several treatments applied at daily intervals for approximately one week result in the complete elimination of the spider veins; relatively larger vessels may likely require a longer treatment period and/or a higher concentration of the effective ingredient.

The useful compounds are low molecular weight organic acids selected preferably from the phosphoryl derivatives of inositol, including the mono-, di-, tri-, tetra-, penta- and hexaphosphate derivatives of inositol. Inositol is also known as 1,2,3,4,5,6-hexahydroxycyclohexane and 1,2,3,4,5,6-cyclohexanehexol. An especially preferred compound is inositol hexaphosphate, otherwise known as phytic acid.

Figure 1:
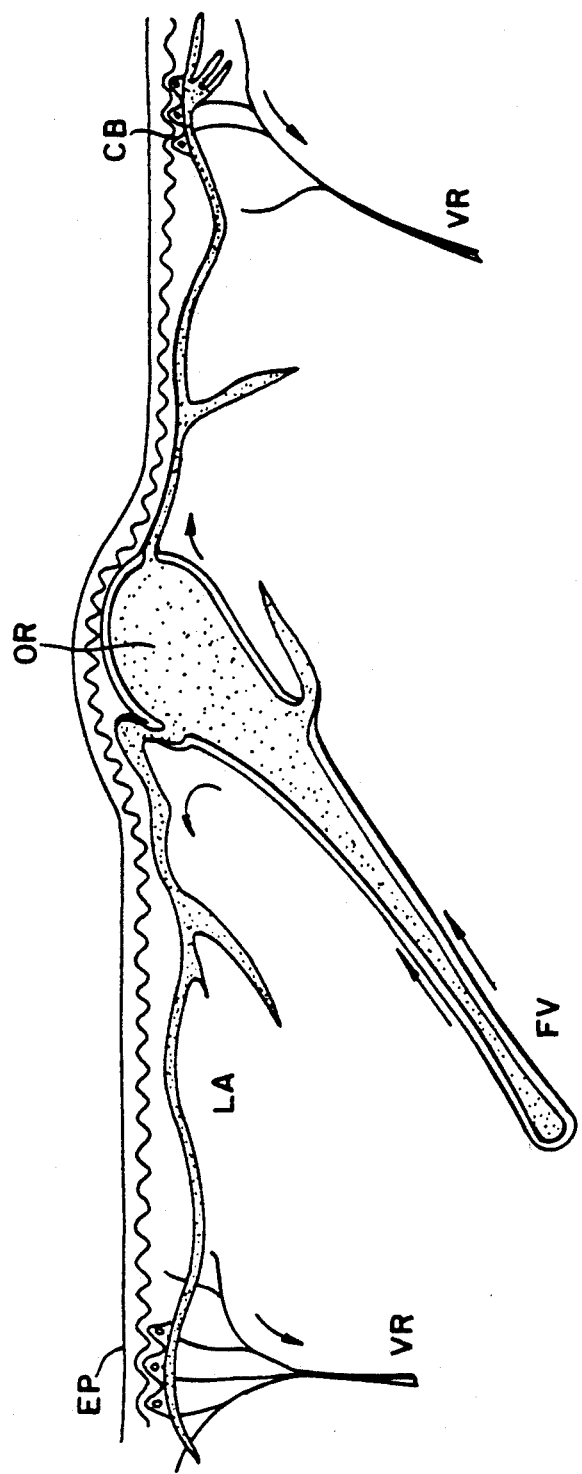
FIG. 1, discussed in the Background section, illustrates the dermatological morphology of a typical spider vein.
Figure 2:
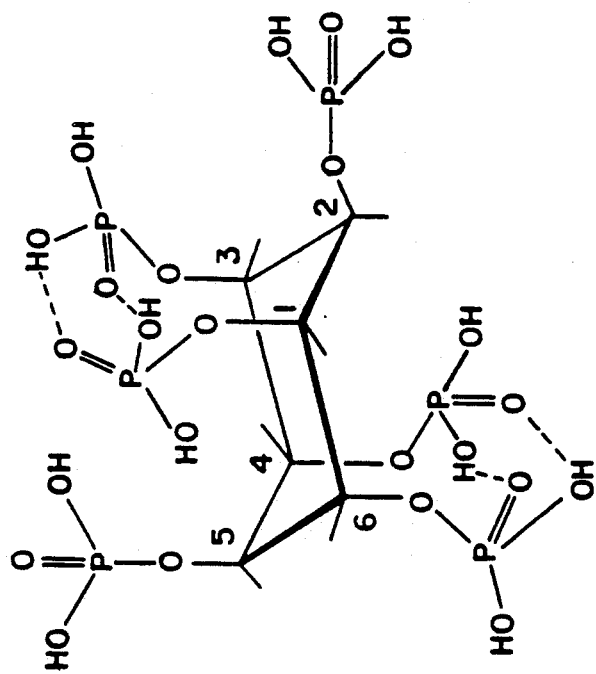
FIG. 2 shows Fisher and Howart projections for phytic acid.
Figure 2:
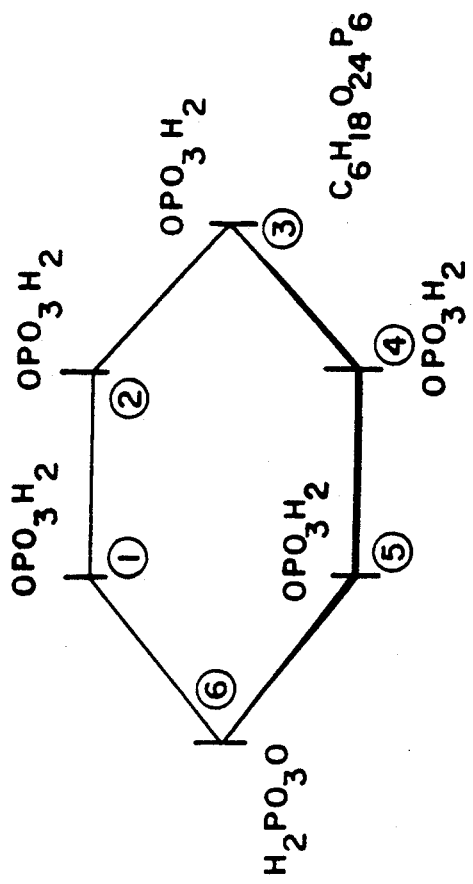

FIG. 2 depicts Fisher and Howart projections of phytic acid. The Howart projection shows the hydrogen bonding interaction among various phosphoryl groups across the ring structure. It is believed that aliphatic and alicyclic compounds having from four to eight carbon atoms and at least two phosphoryl groups may be useful for the treatment of telangestasia. Other acidic derivatives, such as sulfuryl and carboxyl, may also be effective. As used herein, inositol phosphoric acid or and derivatives and mixtures thereof include molecules having an inositol ring with at least two phosphoryl groups attached thereto.

The efficacy of phytic acid, and generally inositol phosphoric acid and its derivatives, is partially provided by two characteristics of the molecule. One characteristic is the presence of hydroxyl groups in the vicinity of the proton donor. As shown in FIG. 2, the hydroxyl portion of the phosphoryl groups can hydrogen-bond to the keto portion of an adjacent phosphoryl group. The hydroxyl groups may allow the molecule to readily penetrate the most superficial layers of skin which are slightly polar because they lack a significant phospholipid concentration.

Another beneficial characteristic is the ability of these compounds to yield protons, thereby remaining polar over a wide range of pH values. For example, it has been reported in the literature (e.g., W. J. Evans, JAOCS, Vol. 59, No. 4, Apr. 1982) that phytic acid (hexainositol phosphate) has twelve distinct pK values equally distributed between pH 1.1 and pH 12.0. Once a highly polar molecule reaches viable tissue, it will be repulsed by cell membrane phospholipids and remain in the intercellular space. Instead of being lost through dissipation, the molecules remain sequestered and form a stable depot, which creates a high osmotic gradient necessary for the collapse of an offending vessel. This osmotic gradient is analogous to that created when hypertonic saline is used invasively as a sclerosing agent.

An effective amount of the low molecular weight organic acid is at least 3 percent, by weight or volume. Weight and volume fractions are often similar because the components of any formulation have densities within 20 percent of one another. Effective amounts will necessarily depend on end-use conditions, as well as the condition of an offending vessel. For example, a skilled dermatologist may use compositions containing 70–100 percent phytic acid for a period of 30 seconds to 3 minutes. Over-the-counter compositions would preferably contain a lower concentration to permit retail application without fear of skin damage. For these applications, concentrations of about 5–50 percent are preferred, with 15–30 percent more preferred.

According to the present invention, active ingredient(s) may be uniformly dispersed in a cream, lotion, ointment or simple phase solution. The active ingredient is dispersed in a cosmetic composition by conventional methods known in the art.

The pH of the composition can be adjusted with suitable organic and/or inorganic buffers. Organic buffers are typically primary, secondary and tertiary amines. Inorganic buffers may include potassium hydroxide, sodium hydroxide and ammonium hydroxide. An active ingredient may also be reacted with a selected amine to provide a buffering moiety directly on the active ingredient molecule.

The composition may also include the active ingredient(s) in combination with one or more cosmetically acceptable vasoactive agents. Preferred vasoactive agents include xanthine and other alkaloids and their derivatives, as well as other classes of sympathomimetics. More preferably, the composition may include a vasodilatory agent such as methylnicotinate. Vasodilators generally increase the size of the treated vessel and, in turn, the tissue area available for interaction with the anti-telangiectatic agent.

Further additions are contemplated provided that they are compatible with the active ingredient(s) and do not adversely affect the desired function. Exemplary additives include pigments and colorants, fragrances, emollients, moisturizers, antiseptics, astringents and the like which perform a cosmetic or maintenance function on the skin.

The invention will now be further described with reference to the following examples which are provided for illustrative, not limiting purposes.

EXAMPLE I

A composition was prepared according to conventional cosmetic techniques.

|  | % (w/w) |
| --- | --- |
| deionized water | 57.60 |
| inositol hexaphosphate (phytic acid) | 35.00 |
| glycerin | 3.00 |
| sodium ethylene diamino tetraacetic acid | 0.15 |
| beeswax | 0.25 |
| sesame oil | 1.00 |
| sodium phosphate monobasic | 0.25 |
| isopropyl myristate | 1.00 |
| palm oil | 1.00 |
| light mineral oil | 0.75 |

EXAMPLE II

Using similar cosmetic formulation techniques, the following composition was prepared.

|  | % (w/w) |
| --- | --- |
| deionized water | 57 |
| propylene glycol | 15 |
| inositol hexaphosphate | 18 |
| ethanol | 10 |

Subjects were selected based on the presence of spider veins as established by previously defined criteria. The compositions of Examples I and II were applied to areas showing well-defined, macroscopically visible spider veins. The application was performed with a cotton swab soaked in each composition. After approximately one minute of gentle swabbing, some minor skin discomfort was felt by the subjects. After three to five days of consecutive applications, the treated spider veins were distinctively less visible or had disappeared completely. Control (untreated) spider veins remained unchanged.

A second embodiment of the present invention includes the use of a compression bandage or stocking in combination with an effective amount of inositol phosphoric acid and/or derivative compositions. This embodiment involves use of a compression bandage to maintain pressure on the skin for a period of time after initial application of an effective compound. The compression bandage may be removed daily for reapplication of the topical composition.

It is believed that a compression bandage applies pressure which maintains the offending vessel in a collapsed condition so that the repair process does not produce an open vessel. Bandages or stockings are likely to facilitate treatment for relatively large vessels normally found in the legs. A compression bandage also may be used when normal, unaided treatment is ineffective, or when a vein reappears after initial treatment. In any event, the compression bandage is applied until the natural healing process has been completed.

This specification clearly illustrates the principles of the present invention. Based on this disclosure, numerous modifications will be readily apparent to those skilled in the art. These modifications are within the scope and spirit of the present invention as defined by the following claims.

What is claimed is:

1. A method for treating telangiectasia which comprises the topical application of a composition to an area affected by telangiectasia, wherein said composition includes an effective amount of a member selected from the group consisting of inositol phosphoric acid, its sulfuryl derivative and its carboxyl derivative and mixtures thereof in the range from about 3 percent to about 100 percent.

2. The method of claim 1, wherein said derivative is inositol hexaphosphate (phytic acid).

3. The method of claim 1, wherein said effective amount is at least 3 percent.

4. The method of claim 1, wherein said effective amount is in the range from about 5 percent to about 50 percent.

5. The method of claim 4, wherein said effective amount is in the range from about 15 percent to about 30 percent.

6. The method of claim 1, which further comprises daily topical applications for a period of two to 14 days.

7. The method of claim 1, which further comprises application of a compression bandage.

8. The method of claim 1, wherein said composition further comprises a vasoactive agent.

9. The method of claim 1, wherein said composition further comprises a buffering agent.

* * * * *